US00PP26932P2

(12) United States Plant Patent
Li

(10) Patent No.: US PP26,932 P2
(45) Date of Patent: Jul. 12, 2016

(54) *VERBENA* PLANT NAMED 'KLEVP14490'

(50) Latin Name: ***Verbena* sp.**
Varietal Denomination: KLEVP14490

(71) Applicant: Klemm+Sohn GmbH & Co. KG, Stuttgart (DE)

(72) Inventor: Ruijun Li, North Parramata (AU)

(73) Assignee: Klemm + Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 14/545,038

(22) Filed: Mar. 19, 2015

(51) Int. Cl.
*A01H 5/02* (2006.01)

(52) U.S. Cl.
USPC ..... Plt./308

(58) Field of Classification Search
USPC ..... Plt./308
CPC ..... A01H 5/02
See application file for complete search history.

*Primary Examiner* — Kent L Bell
(74) *Attorney, Agent, or Firm* — James M. Weatherly; Bethany R. Roahrig; Cochran Freund & Young, LLC

(57) ABSTRACT

A new *Verbena* plant particularly distinguished by a red flower color with small white eyes, large flower size and good resistance to powdery mildew, is disclosed.

1 Drawing Sheet

Genus and species: *Verbena* sp.
Variety denomination: 'KLEVP14490'.

BACKGROUND OF THE NEW PLANT

The present invention comprises a new and distinct variety of *Verbena*, botanically known as *Verbena* sp., and hereinafter referred to by the variety name 'KLEVP14490'. 'KLEVP14490' originated from a cross-pollination conducted in September 2009 in Cobbitty, Australia between the proprietary female *Verbena* variety 'V975' (unpatented), and the proprietary male *Verbena* variety 'V980' (unpatented).

The seeds from the cross were sown and plants were grown for evaluation, where an individual plant designated 'KLEVP14490' was selected from the group of plants in Cobbitty, NSW, Australia in April 2010.

In April 2010, 'KLEVP14490' was first vegetatively propagated by vegetative cuttings in Cobbitty, NSW, Australia. 'KLEVP14490' was found to reproduce true to type in successive generations of asexual propagation via vegetative cuttings.

SUMMARY

The following are the most outstanding and distinguishing characteristics of this new variety when grown under normal horticultural practices in Cobbitty, Australia.

1. Red flower color with small white eyes;
2. Large flower size; and
3. Good resistance to powdery mildew.

DESCRIPTION OF THE PHOTOGRAPH

This new *Verbena* plant is illustrated by the accompanying photograph, which shows the plant grown in a pot. The photograph is of a three-month-old plant grown in Stuttgart, Germany in May 2014. The colors shown are as true as can be reasonably obtained by conventional photographic procedures.

DESCRIPTION OF THE NEW VARIETY

The following detailed descriptions set forth the distinctive characteristics of 'KLEVP14490'. The data which define these characteristics were collected from asexual reproductions carried out in Cobbitty, Australia. Data was collected on three-month-old plants grown in a greenhouse in Cobbitty, Australia in February 2015. Color references are to The R.H.S. Colour Chart of The Royal Horticultural Society of London (R.H.S.)(2005).

Classification:
- *Family*.—Verbenaceae.
- *Botanical*.—*Verbena* sp.
- *Common*.—*Verbena*.
- *Designation*.—'KLEVP14490'.

Parentage:
- *Female parent*.—The proprietary female *verbena* variety 'V975' (unpatented).
- *Male parent*.—The proprietary male *verbena* variety 'V980' (unpatented).

Plant:
- *Growth and branching habit*.—Semi-upright.
- *Height (from top of soil)*.—30.0 cm.
- *Width (horizontal plant diameter)*.—30.0 cm.
- *Time to produce a finished flowering plant*.—Approximately 8 weeks.
- *Time to initiate and develop roots*.—3 weeks.
- *Root description*.—White.

Stems:
- *Number of branches per plant*.—More than 35.
- *Growth habit*.—Semi-upright.
- *Length*.—20.0 cm.
- *Diameter*.—1.0 cm.
- *Internode length*.—Approximately 2.0 cm.
- *Color*.—RHS 130D.
- *Anthocyanin*.—Absent.
- *Texture and appearance*.—Pubescence, round.

Leaves:
- *Arrangement*.—Opposite.
- *Immature and mature leaf*.—Color: Upper surface: RHS 141A. Lower surface: RHS 141C.
- *Length*.—2.5 cm.
- *Width*.—1.5 cm.
- *Shape*.—Lanceolate.

*Apex*.—Acute.
*Base*.—Obtuse.
*Margin*.—Crenate.
*Texture*.—Upper surface: Leathery. Lower surface: Rugose.
*Venation type*.—Pinnate.
*Venation color*.—Upper and lower surfaces: RHS 141D.
*Petioles*.—Length: 0.4 cm. Diameter: 0.1 cm. Color: RHS 141D. Texture: Leathery.

Flower buds:
*Shape*.—Tall, cylindrical.
*Length*.—0.5 cm.
*Diameter*.—0.1 cm.
*Color* (*at tight bud*).—RHS 49A.

Inflorescence:
*Blooming habit* (*flowering season*).—Continuously.
*Lastingness of individual blooms on the plant*.—2 weeks.
*Fragrance*.—Absent.
*Inflorescence type*.—Umbel.
*Length of inflorescence*.—6.0 cm.
*Diameter of inflorescence*.—6.0 cm.
*Number of florets per inflorescence*.—More than 15.
*Peduncle*.—Color: RHS 141A. Length: 1.0 cm. Diameter: 0.1 cm.

Florets:
*Length*.—2.0 cm.
*Diameter*.—4.0 cm.
*Texture*.—Glossy.
*Form*.—Single.
*Length*.—1.0 cm.
*Diameter*.—3.0 cm.
*Color*.—Immature: Upper surface: RHS 41A. Lower surface: RHS 52B. Mature: Upper surface: RHS 50B. Lower surface: RHS 51B.
*Corolla tube length*.—1.2 cm.
*Corolla tube color*.—RHS 56C.
*Petals*.—Length of lobe: 2.0 cm. Diameter of lobe: 2.0 cm. Lobe shape: Round. Apex: Acute. Base: Obtuse. Margin: Entire. Texture: Upper and lower surfaces: Glossy, satiny.
*Pedicels*.—Not visible.

Sepals:
*Shape*.—Lanceolate.
*Apex*.—Acute.
*Base*.—Obstuse.
*Margin*.—Entire.
*Length*.—2.0.
*Diameter*.—0.5 cm.
*Color*.—RHS 141C.
*Texture*.—Upper and lower surfaces: Hairy, dull.

Reproductive organs:
*Stamens*.—Present.
*Quantity*.—4.
*Color*.—RHS 139D.
*Filament length*.—0.6 cm.
*Filament diameter*.—0.1 cm.
*Anther*.—Shape: Elliptic. Color: RHS 141D. Length: 0.8 cm. Diameter: 0.2 cm.
*Pollen amount*.—Sparse.
*Pistils*.—Number: 1. Length: 1.0 cm.
*Diameter*.—0.1 cm.
*Stigma*.—Color: RHS 141D. Appearance: Ovate. Length: 0.1 cm. Diameter: 0.1 cm.
*Style*.—Color: RHS 141D. Length: 0.9 cm. Diameter: 0.1 cm. Appearance: Long.

Fruit and seed set: None observed.

Disease and pest/insect resistance: Good resistance to powdery mildew.

COMPARISON WITH PARENTAL LINES AND KNOWN VARIETIES

'KLEVP14490' is distinguished from its parents as described in Table 1.

TABLE 1

Comparison with Parental Lines

| Trait | Variety 'KLEVP14490' | Female parent 'V975' | Male parent 'V980' |
|---|---|---|---|
| Flower color | Red with small white eyes | Pink with large white eyes | Solid burgundy |
| Flower size | Large | Large | Medium |

'KLEVP14490' is most similar to the commercial *verbena* Empress Red (patent status unknown). Differences between the varieties are described in Table 2.

TABLE 2

Comparison with Similar Variety

| Trait | Variety 'KLEVP14490' | Commercial line Empress Red |
|---|---|---|
| Flower color | Red with small white eyes | Solid red |
| Flower size | Large | Medium |
| Resistance to powdery mildew | Good resistance | Less resistance than 'KLEVP14490' |

I claim:

1. A new and distinct variety of *Verbena* plant designated 'KLEVP14490' as illustrated and described herein.

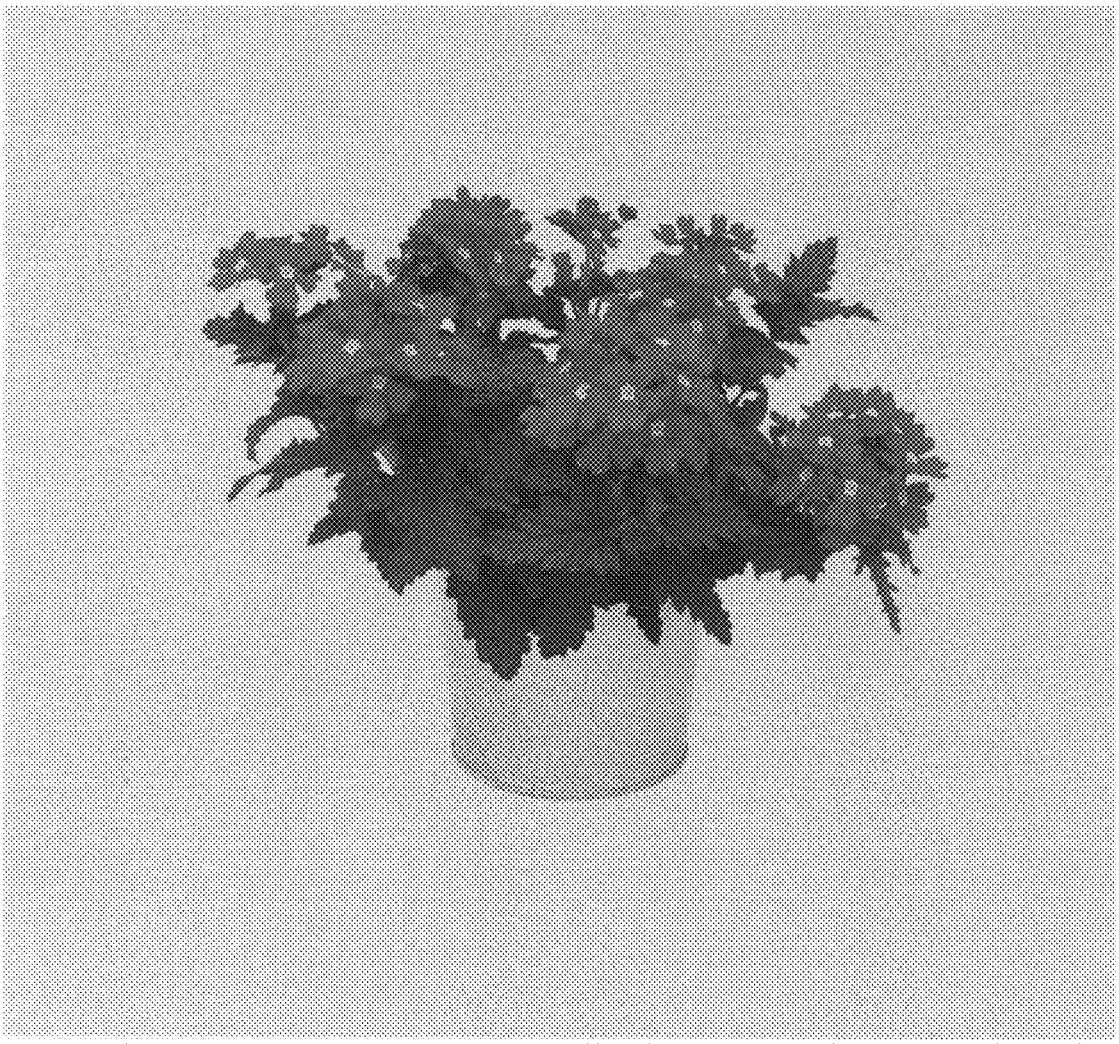

* * * * *